(12) United States Patent
Shimada et al.

(10) Patent No.: US 7,915,477 B2
(45) Date of Patent: Mar. 29, 2011

(54) DISPOSABLE WEARING ARTICLE

(75) Inventors: Takaaki Shimada, Kagawa-ken (JP); Junko Sato, Kagawa-ken (JP)

(73) Assignee: Uni-Charm Corporation, Ehime (JP)

( * ) Notice: Subject to any disclaimer, the term of this patent is extended or adjusted under 35 U.S.C. 154(b) by 181 days.

(21) Appl. No.: 12/285,959

(22) Filed: Oct. 17, 2008

(65) Prior Publication Data

US 2009/0062759 A1    Mar. 5, 2009

Related U.S. Application Data

(62) Division of application No. 10/967,148, filed on Oct. 19, 2004, now Pat. No. 7,527,617.

(30) Foreign Application Priority Data

Oct. 24, 2003   (JP) ................................ 2003-364338

(51) Int. Cl.
*A61F 13/58* (2006.01)
(52) U.S. Cl. ................. 604/365; 604/389; 604/396
(58) Field of Classification Search ............. 604/365, 604/370, 385.23, 389–391, 396
See application file for complete search history.

(56) References Cited

U.S. PATENT DOCUMENTS

| | | | |
|---|---|---|---|
| 2,705,687 A * | 4/1955 | Petterson et al. | 428/198 |
| 3,009,822 A * | 11/1961 | Griswold et al. | 428/195.1 |
| 3,575,764 A * | 4/1971 | McFarren | 156/306.6 |
| 3,783,871 A | 1/1974 | Sabee | |
| 3,874,386 A | 4/1975 | Kozak | |
| 3,949,128 A * | 4/1976 | Ostermeier | 428/152 |
| 4,177,812 A | 12/1979 | Brown et al. | |
| 4,237,890 A | 12/1980 | Laplanche | |
| 4,275,105 A * | 6/1981 | Boyd et al. | 428/198 |
| 4,317,449 A | 3/1982 | Nowakoski | |
| 4,576,600 A | 3/1986 | Joa | |
| 4,643,729 A * | 2/1987 | Laplanche | 604/389 |
| 4,663,220 A | 5/1987 | Wisneski et al. | |
| 4,670,012 A | 6/1987 | Johnson | |
| 5,182,156 A | 1/1993 | Pape et al. | |
| 5,226,992 A | 7/1993 | Morman | |
| 5,246,433 A | 9/1993 | Hasse et al. | |
| 5,279,604 A | 1/1994 | Robertson et al. | |
| 5,531,732 A | 7/1996 | Wood | |

(Continued)

FOREIGN PATENT DOCUMENTS

EP    0531666 A1    3/1993

(Continued)

OTHER PUBLICATIONS

European Search Report issued Sep. 9, 2009.

*Primary Examiner* — Tatyana Zalukaeva
*Assistant Examiner* — Paula L Craig
(74) *Attorney, Agent, or Firm* — Lowe, Hauptman, Ham & Berner, LLP (57) ABSTRACT

A disposable wearing article has its outer surface formed from a nonwoven fabric of thermoplastic synthetic fibers. A tape strip constituting each of the tape fasteners is folded in Z- or inverted Z-shape and attached in such folded state to the outer surface of the wearing article by means of first adhesive. As for a spot at which the tape strip is attached to the outer surface of the wearing article, the nonwoven fabric at least partially presents a film-like outer surface.

14 Claims, 6 Drawing Sheets

U.S. PATENT DOCUMENTS

| | | |
|---|---|---|
| 5,537,722 A | 7/1996 | Niederhofer et al. |
| 5,591,521 A | 1/1997 | Arakawa et al. |
| 5,605,735 A | 2/1997 | Zehner et al. |
| 5,618,366 A | 4/1997 | Suekane |
| 5,624,428 A | 4/1997 | Sauer |
| 5,626,574 A | 5/1997 | Sasaki et al. |
| 5,629,063 A | 5/1997 | Gobran |
| 5,662,638 A | 9/1997 | Johnson et al. |
| 5,695,868 A | 12/1997 | McCormack |
| 5,830,206 A | 11/1998 | Larsson |
| 5,860,964 A | 1/1999 | Willekens et al. |
| 5,989,478 A | 11/1999 | Ouellette et al. |
| 5,990,377 A | 11/1999 | Chen et al. |
| 5,997,981 A | 12/1999 | McCormack et al. |
| 6,049,023 A | 4/2000 | Blenke et al. |
| 6,063,065 A | 5/2000 | Costa |
| 6,075,178 A | 6/2000 | La Wilhelm et al. |
| 6,102,901 A | 8/2000 | Lord et al. |
| 6,123,694 A | 9/2000 | Pieniak et al. |
| 6,159,584 A | 12/2000 | Eaton et al. |
| 6,159,881 A | 12/2000 | Datta et al. |
| 6,191,055 B1 | 2/2001 | Boyer, III et al. |
| 6,264,644 B1 | 7/2001 | Igaue et al. |
| 6,307,120 B1 | 10/2001 | Glaug |
| 6,328,725 B2 | 12/2001 | Fernfors |
| 6,371,949 B1 | 4/2002 | Soga et al. |
| 6,387,085 B1 | 5/2002 | Van Gompel et al. |
| 6,475,205 B2 | 11/2002 | Shimada et al. |
| 6,508,797 B1 | 1/2003 | Pozniak et al. |
| 6,524,293 B1 | 2/2003 | Elsberg et al. |
| 6,526,631 B1 | 3/2003 | Alberg et al. |
| 6,531,207 B1 | 3/2003 | Eaton et al. |
| 6,551,294 B1 | 4/2003 | Elsberg et al. |
| 6,572,601 B2 | 6/2003 | Suprise et al. |
| 6,579,275 B1 | 6/2003 | Pozniak et al. |
| 6,596,107 B2 | 7/2003 | Stopher |
| 6,620,490 B1 * | 9/2003 | Malchow et al. ............ 428/196 |
| 6,638,261 B2 | 10/2003 | Suzuki |
| 6,645,189 B2 | 11/2003 | Kurita et al. |
| 6,649,001 B2 | 11/2003 | Heden et al. |
| 6,656,171 B1 * | 12/2003 | Matsuda et al. ............ 604/390 |
| 6,682,626 B2 | 1/2004 | Mlinar et al. |
| 6,713,159 B1 * | 3/2004 | Blenke et al. ............ 428/195.1 |
| 6,726,670 B2 | 4/2004 | Almberg et al. |
| 6,740,071 B2 | 5/2004 | Gibbs |
| 6,838,591 B2 | 1/2005 | Waksmundzki et al. |
| 6,869,659 B2 | 3/2005 | Shepard et al. |
| 6,926,704 B2 | 8/2005 | Andersson et al. |
| 6,972,012 B1 | 12/2005 | Pozniak et al. |
| 7,056,313 B2 * | 6/2006 | Franke et al. ............ 604/396 |
| 7,132,031 B2 | 11/2006 | Ohiro et al. |
| 7,322,968 B2 | 1/2008 | Shimoe |
| 7,527,617 B2 * | 5/2009 | Shimada et al. ............ 604/389 |
| 2001/0011168 A1 | 8/2001 | Shimada et al. |
| 2002/0026172 A1 | 2/2002 | Shimada et al. |
| 2002/0035354 A1 | 3/2002 | Mirle et al. |
| 2002/0052593 A1 | 5/2002 | Kurita et al. |
| 2002/0173765 A1 * | 11/2002 | Pargass et al. ............ 604/386 |
| 2003/0014030 A1 | 1/2003 | Andersson et al. |
| 2003/0219594 A1 | 11/2003 | Qin et al. |
| 2004/0138639 A1 | 7/2004 | Ito et al. |
| 2004/0167486 A1 | 8/2004 | Busam et al. |
| 2004/0194879 A1 | 10/2004 | Ohiro et al. |
| 2004/0267227 A1 | 12/2004 | Ito et al. |
| 2005/0038405 A1 | 2/2005 | Shimoe |
| 2005/0070868 A1 | 3/2005 | Ito et al. |
| 2005/0101926 A1 | 5/2005 | Ausen et al. |
| 2005/0124950 A1 * | 6/2005 | Sasaki et al. ............ 604/367 |
| 2005/0256477 A1 | 11/2005 | Van Gompel et al. |
| 2006/0206092 A1 | 9/2006 | Shimoe |

FOREIGN PATENT DOCUMENTS

| | | |
|---|---|---|
| EP | 0 815 820 A2 | 1/1998 |
| EP | 0623330 A2 | 11/2008 |
| GB | 1441567 | 7/1976 |
| JP | 50109041 A | 8/1975 |
| JP | 24372 A | 1/1990 |
| JP | 3165763 A | 7/1991 |
| JP | 539531 U | 5/1993 |
| JP | 677719 U | 11/1994 |
| JP | 8507699 | 8/1996 |
| JP | 9253125 A | 9/1997 |
| JP | 10085254 | 4/1998 |
| JP | 10211231 A | 8/1998 |
| JP | 2000502573 | 3/2000 |
| JP | 2001046436 A | 2/2001 |
| JP | 2001079036 A | 3/2001 |
| JP | 2001178777 | 7/2001 |
| WO | 9409736 A1 | 5/1994 |
| WO | 0113842 A1 | 3/2001 |
| WO | 03022195 A1 | 3/2003 |
| WO | 03/079952 A1 | 10/2003 |

* cited by examiner

DISPOSABLE WEARING ARTICLE

RELATED APPLICATIONS

The present application is a divisional of U.S. application Ser. No. 10/967,148, filed Oct. 19, 2004, and claims priority from Japanese Application Number 2003-364338 filed Oct. 24, 2003, the disclosures of which are hereby incorporated by reference herein in their entirety.

BACKGROUND OF THE INVENTION

The present invention relates to disposable wearing articles and more preferably to such articles provided with tape fasteners and adapted to be suitably used as diapers or the like.

U.S. Pat. No. 4,237,890 (Citation 1) discloses a fastening means used for a disposable diaper comprising a tape strip folded with extendability in S- or Z-shape. This tape strip has a first end portion fixed to an outer surface of the diaper by means of first pressure-sensitive adhesive and a second end portion opposed to the first end portion wherein the second end portion may be pulled to unfold and thereby to extend the tape strip. The second end portion is coated on its inner surface with second pressure-sensitive adhesive.

U.S. Pat. No. 5,182,156 (Citation 2) also discloses a fastening means comprising a tape strip folded in Z-shape. This tape fastener is used in a manner similar to that in which the tape fastener disclosed in Citation 1 is used.

Japanese Laid-Open Patent Application Gazette No. 1990-4372 (Citation 3) discloses a disposable absorbent product provided with a fastener system. This fastener system comprises a Y-shaped tape strip.

For the tape strip disclosed in Citation 1 and 2 normally folded in S- or Z-shape before actually used, it is likely that the tape strip might be easily peeled off from the outer surface of the diaper under a peeling force generated between the tape strip and the outer surface of the diaper as the tape strip is unfolded and extended. It will be effective to enhance an adhesive force of the pressure-sensitive adhesive for the purpose of preventing such peeling off of the tape strip. However, if the tape strip having such a high adhesive force is attached to the outer surface of the diaper formed from a nonwoven fabric, texture of the nonwoven fabric, more specifically, intertwined component fibers constituting the nonwoven fabric may be disentangled as the tape strip is pulled outward and the tape strip may fall off from the diaper together with these disentangled component fibers.

The Y-shaped tape strip used for the product disclosed in Citation 3 is attached to both the outer surface and the inner surface of the diaper by means of pressure-sensitive adhesive coated on this tape strip to prevent the tape strip from readily falling off from the diaper as the tape strip is pulled outward. However, depending on the design, such Y-shape tape strip generally has poor extendability compared to the tape strip folded in S- or Z-shape.

SUMMARY OF THE INVENTION

It is an object to provide a disposable wearing article having an outer surface defined by a nonwoven fabric improved so that the fastener tape folded in Z- or inverted Z-shape attached to the outer surface of the wearing article can be reliably prevented from falling off from the wearing article even when the tape strip is pulled outward for actual use thereof.

The present invention is directed to a disposable wearing article having a crotch region, a front waist region extending forward from the crotch region and a rear waist region extending rearward from the crotch region, each of these regions having inner and outer surfaces, a pair of transversely opposite lateral edge portions extending in parallel to each other in back-and-forth direction of the crotch region, the front and rear waist regions further including respective upper end portions extending in a transverse direction of the crotch region between the transversely opposite lateral edge portions, and the front waist region or the rear waist region having, on an outer surface in a vicinity of the lateral edge portions and/or the upper end portion, tape fasteners each comprising a tape strip folded in Z- or inverted Z-shape with extendability and a fastening means provided on the tape strip.

The wearing article according to the present invention further comprises the outer surfaces of the front and rear waist regions being formed from a nonwoven fabric of thermoplastic synthetic fibers, the tape strip of the tape fastener having a surface thereof facing the nonwoven fabric bonded to the nonwoven fabric by means of adhesive and, in the nonwoven fabric, a spot destined to be bonded to the tape strip at least partially presents a film-like outer surface formed by a plurality of the synthetic fibers fused together.

The tape fastener for the disposable wearing article has its tape strip bonded to the nonwoven fabric defining the outer surface of the wearing article by means of adhesive wherein the spot at which the tape strip is bonded has been transformed to the film-like state. In this way, there is no anxiety that the nonwoven fabric's texture might be destroyed and the tape fastener might fall off from the wearing article as the tape fastener is forcefully pulled outward.

According to one preferred embodiment of the invention, the nonwoven fabric has a basis weight in a range of about 10 to about 50 g/m$^2$. Even when the outer surface of the wearing article is formed by the nonwoven fabric having such basis weight as small as in the range of about 10 to about 50 g/m$^2$, it is ensured to eliminate an anxiety that the nonwoven fabric's texture might be destroyed and the tape fastener might fall off from the wearing article.

According to another preferred embodiment of the invention, the wearing article is of pants-type formed by the front and rear waist region put flat and heat-sealed at spots arranged along respective lateral edge portions and, in each of these heat-sealed spots, the synthetic fibers form the film-like outer surface and the tape strip is bonded to this film-like outer surface. In the case of the wearing article according to this embodiment, it is unnecessary to form the film-like outer surface by locally transforming the nonwoven fabric merely for the purpose of attaching the tape fastener to the article. It is for the reason that the film-like outer surface formed when the front and rear waist regions has been bonded to each other along the respective transversely opposite lateral edge portions may be utilized for attachment of the tape fastener.

According to still another preferred embodiment of the invention, the nonwoven fabric presents the film-like outer surface in a region destined to be bonded to the tape strip, at least one of this region's ends opposed as viewed in a direction in which the tape strip is unfolded and extended. According to this embodiment of the tape strip, in a region of the tape strip facing the nonwoven fabric, at least one of this region's opposite ends may be bonded to the film-like outer surface to prevent the tape fastener from falling off from the wearing article.

DETAILED DESCRIPTION OF THE PREFERRED EMBODIMENTS

Details of a disposable wearing article according to the present invention will be more fully understood from the description given hereunder with reference to the accompanying drawings.

Figure 1:
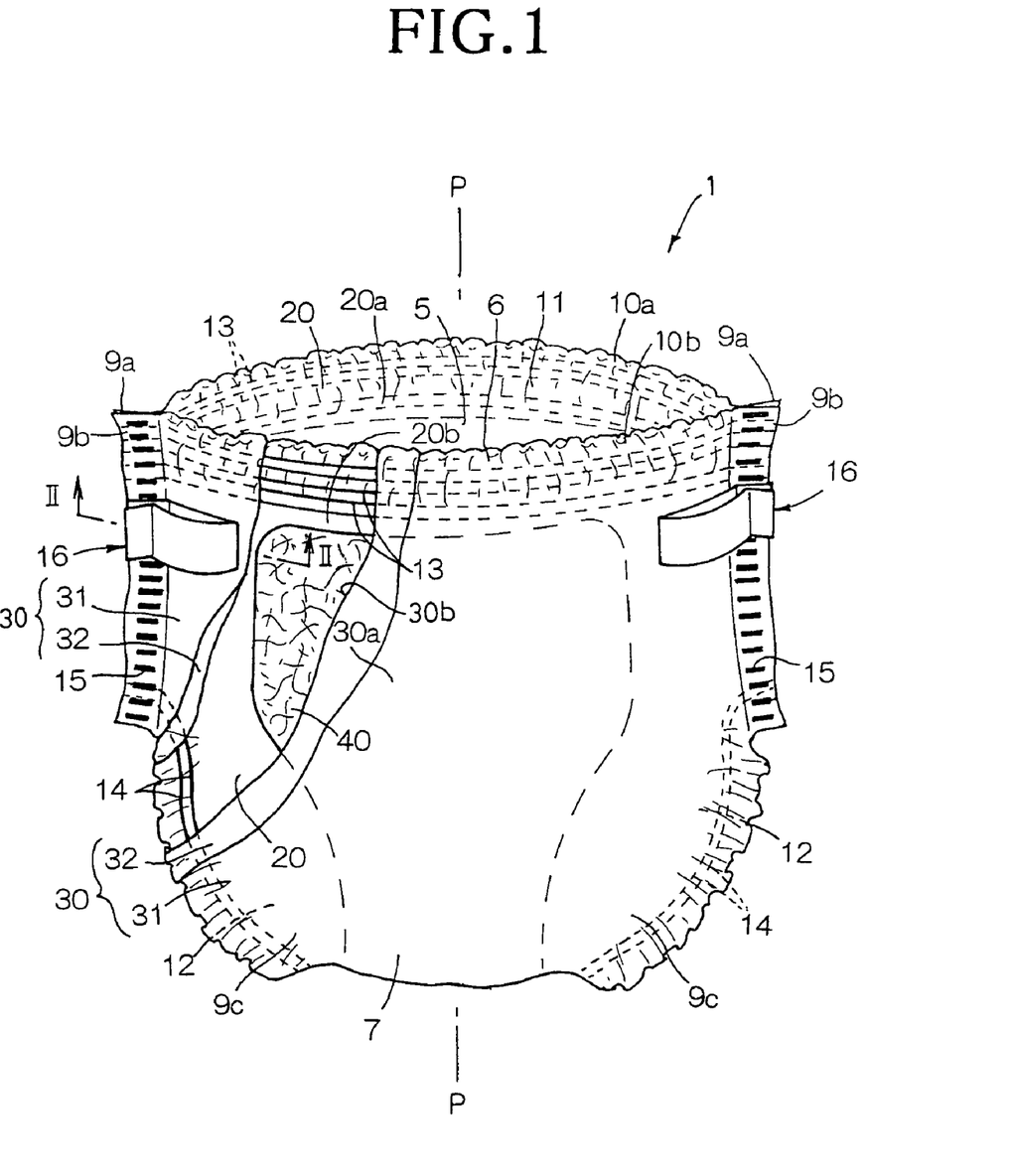
FIG. 1 is a partially cutaway perspective view showing a typical embodiment of a disposable wearing article (disposable diaper) according to the invention.

FIG. 1 is a partially cutaway perspective view showing a disposable pants-type diaper 1 as a typical embodiment of the disposable wearing article according to the invention. The diaper 1 comprises an inner sheet 20 defining an inner surface facing the wearer's skin, an outer sheet 30 defining an outer surface facing the wearer's garment and a liquid-absorbent core 40 interposed between these two sheets 20, 30. The inner sheet 20 is liquid-pervious and formed from a nonwoven fabric made of thermoplastic synthetic fibers or perforated film made of thermoplastic synthetic resin. The inner sheet 20 has an inner surface 20 a and an outer surface 20 b. The outer sheet 30 comprises a first outer sheet 31 formed from a nonwoven fabric of thermoplastic synthetic fibers and a liquid-impervious second outer sheet 32 formed from a film of thermoplastic synthetic resin and intermittently bonded to the inner surface of the first outer sheet 31 by means of hot melt adhesive 2 (See FIG. 2). The first outer sheet 31 defines an outer surface 30 b of the outer sheet 30 and the second outer sheet 32 defines an inner surface 30 a of the outer sheet 30. The core 40 is formed from well known or publicly known absorbent material such as fluff pulp or a mixture of fluff pulp and super-absorbent polymer. As for the configuration, the diaper 1 is composed of a crotch region 7, a front waist region 5 extending forward from the crotch region 7 and a rear waist region 6 extending rearward from the crotch region 7. FIG. 1 illustrates the diaper 1 as viewed from behind, i.e., the rear waist region 6 is seen on this side of the front waist region 5. Respective portions of the inner sheet 20 and the outer sheet 30 extending outward beyond a peripheral edge of the core 40 are put flat together and these portions of the inner sheet 20 and the second outer sheet 32 are heat-sealed or adhesively bonded to each other at bonding spots 3 arranged intermittently in a waist-surrounding direction. Thus, transversely opposite lateral edge portions 9 a, 9 b, 9 c of the front waist region 5, the rear waist region 6 and the crotch region 7 are respectively defined, on one hand, and upper end portions 10 a, 10 b of the front and rear waist regions 5, 6 are respectively defined, on the other hand. The transversely opposite lateral edge portions 9 a of the front waist region 5 and the transversely opposite lateral edge portions 9 b of the rear waist region 6 are put flat and bonded together at bonding spots 15 arranged intermittently in vertical direction of the diaper 1 so as to form a waist-hole 11. At the same time, these transversely opposite lateral edge portions 9 a, 9 b bonded together in this manner cooperate with the crotch region 7 to form a pair of leg-holes 12. Along respective peripheral portions of these waist-hole 11 and leg-holes 12, a plurality of waist-surrounding elastic members 13 and a plurality of leg-surrounding elastic members 14 are interposed between the inner sheet 20 and the outer sheet 30 and bonded in stretched state to the inner surface of at least one of these sheets 20, 30. Tape fasteners 16 are attached to the transversely opposite lateral edge portions 9 b of the rear waist region 6, respectively. These tape fasteners 16 are used to put the front and rear waist regions 5, 6 in close contact with the wearer's waist and/or to hold the used diaper 1 in rolled up state for disposal (See FIG. 4).

Figure 2:
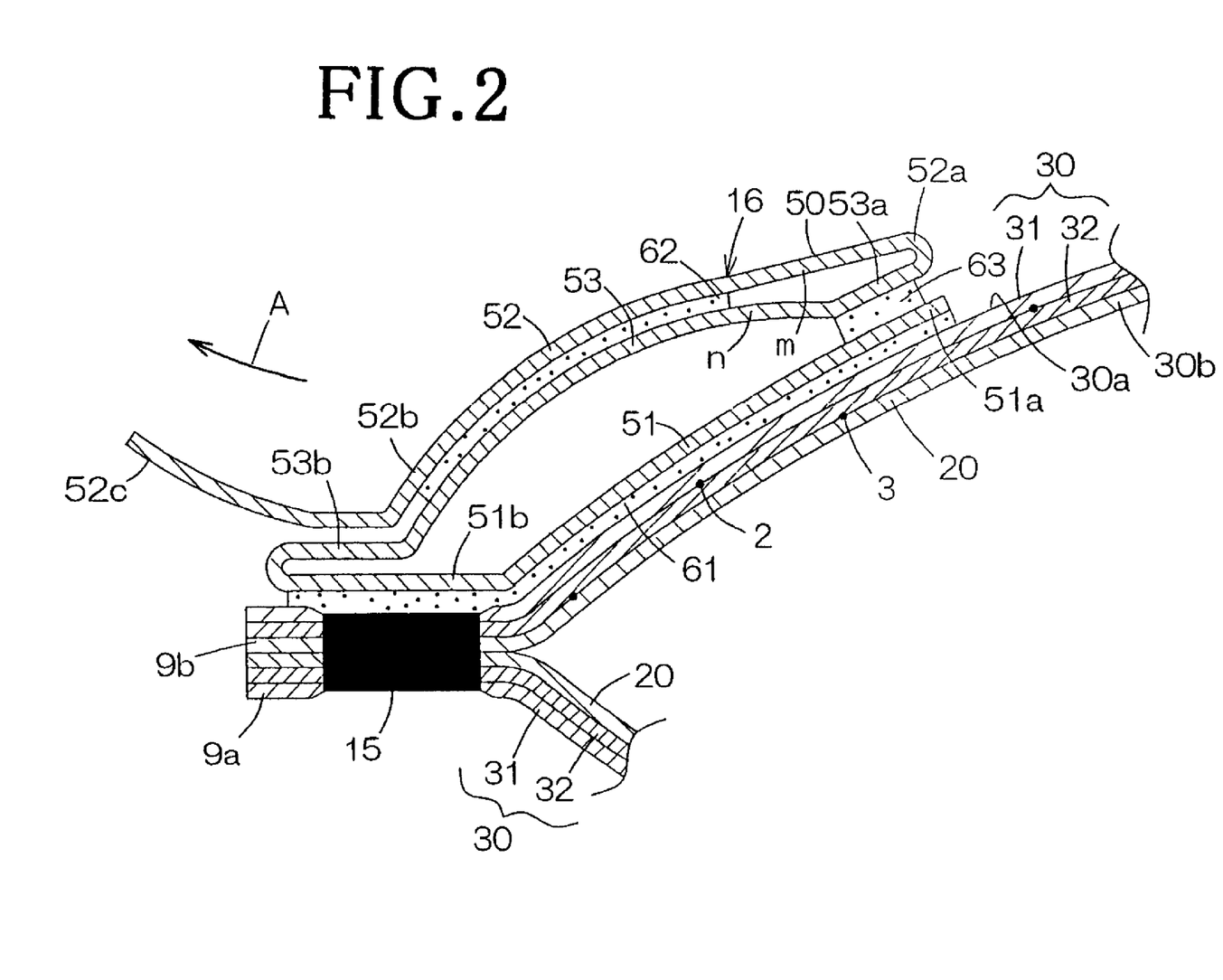
FIG. 2 is a sectional view taken along the line II-II in FIG. 1.

FIG. 2 is a sectional view taken along the line II-II in FIG. 1. The tape fastener 16 is adapted to be folded in Z- or inverted Z-shape as viewed in the waist-surrounding direction before actually used and, in FIG. 2, the tape fastener 16 is illustrated to be folded in Z-shape. The tape fastener 16 is unfolded and extended in its longitudinal direction as the tape fastener 16 is pulled leftward as viewed in FIG. 1, i.e., outward from the associated marginal portion 9b as indicated by an arrow A with a finger-grip 52c held between the fingers (See FIG. 3).

Referring to FIG. 2, the tape fastener 16 comprises a tape strip 50 and fastening means. The tape strip 50 has an inner surface m destined to face the first outer sheet 31 in the unfolded/extended state and an outer surface n opposed to the inner surface m. In the state folded in Z-shape as shown by FIG. 2, the tape strip 50 has a first tape section 51 facing the first outer sheet 31, a second tape section 52 including the finger-grip 52c and a third tape section 53 extending between the first tape section 51 and the second tape section 52. The first tape section 51 has a surface facing the first outer sheet 31 bonded over its whole area to this first outer sheet 31 by means of first adhesive 61. The first tape section 51 has an inner end portion 51a lying aside toward a center line P-P (See FIG. 1) bisecting a width of the diaper 1 and an outer end portion 51b opposed to the inner end portion 51a, i.e., lying aside toward the associated marginal portion 9b. The second tape section 52 has an inner end portion 52a lying aside toward the center line P-P and an outer end portion 52b lying aside toward the associated marginal portion 9b. The finger-grip 52c is contiguous to a distal end of the outer end portion 52b. The third tape section 53 has an inner end portion 53a being contiguous to the inner end portion 52a of the second tape section 52 and an outer end portion 53b which is contiguous to the outer end portion 51b of the first tape section 51. The second tape section 52 is coated on its inner surface m facing the third tape section 53 except the finger-grip 52c and the inner surface m of the inner end portion 52a with second pressure-sensitive adhesive 62 functioning as fastening means. The second tape section 52 is temporarily bonded to the inner surface m of the third tape section 53 by means of the second pressure-sensitive adhesive 62. Of the outer surface n of the third tape section 53 facing the first tape section 51, the outer surface n of the inner end portion 53a is coated with third pressure-sensitive adhesive 63 by means of which the third tape section 53 is temporarily bonded to the outer surface n of the inner end portion 51a of the first tape section 51.

Referring to FIG. 2, the bonding spots 15 at which the front and rear waist regions 5, 6 are bonded to each other along the transversely opposite lateral edge portions 9a, 9b, respectively, may be heated under a pressure or sonic welded to fuse the inner sheet 20, the first outer sheet 31 and the second outer sheet 32 together into a single-layer film at the respective bonding spots 15. At these spots 15, a plurality of component thermoplastic synthetic fibers having constituted nonwoven fabric layers in the inner sheet 20 and the first outer sheet 31, respectively, have no more fibrous form which otherwise could be separated into individual component fibers. The first adhesive 61 serves for permanently bonding the first tape section 51 to the first outer sheet 31 and, by means of this first adhesive 61, the first tape section 51 is bonded not only to the nonwoven fabric in the first outer sheet 31 but also to the bonding spots 15 presenting film-like state.

Figure 3:
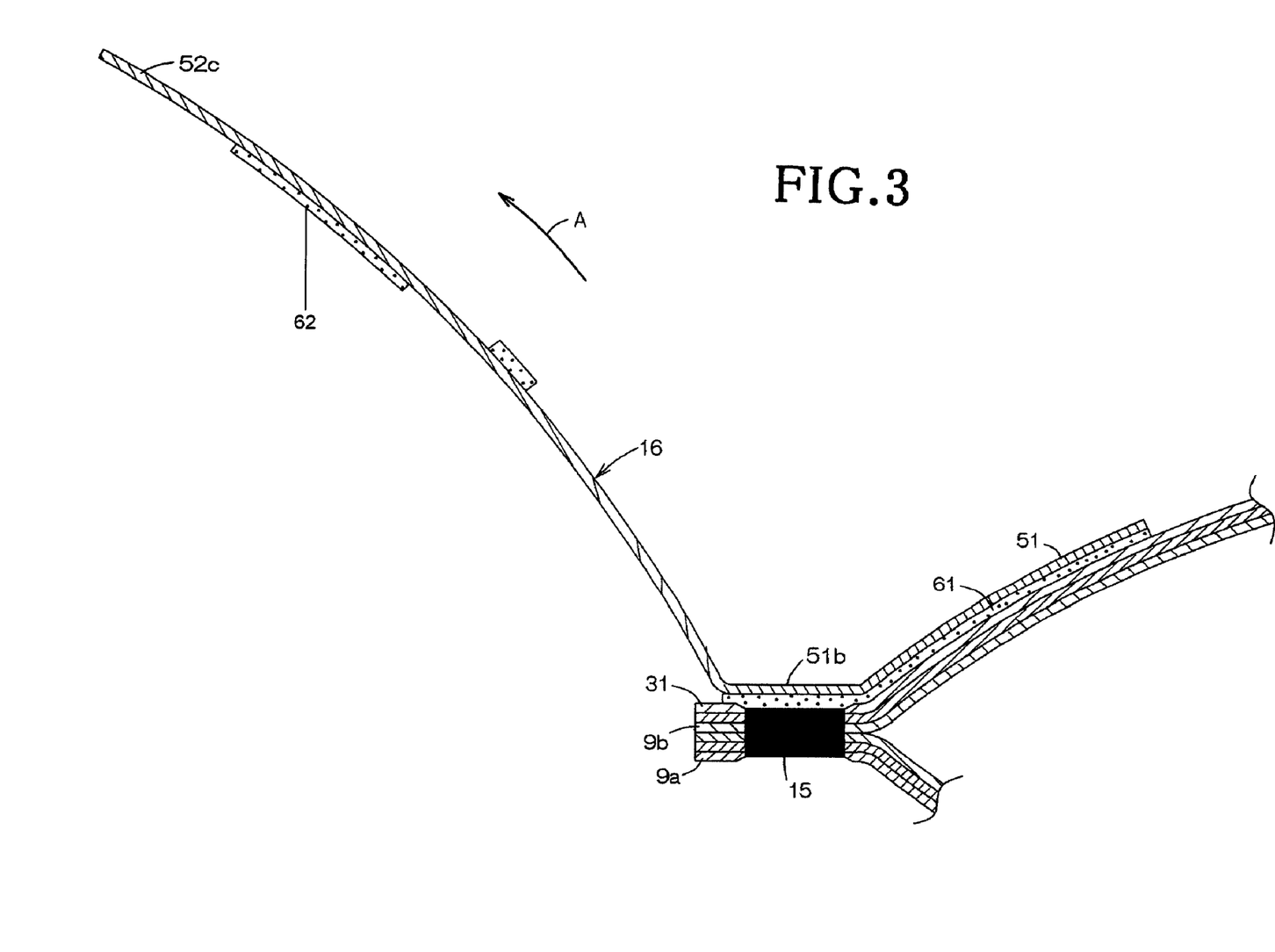
FIG. 3 is a view similar to FIG. 2, showing a tape fastener having been unfolded.

FIG. 3 is a view similar to FIG. 2, showing the tape fastener 16 having been unfolded and extended in the direction indicated by the arrow A. Force intending to peel the outer end portion 51b of the first tape section 51 off from the first outer sheet 31 in the transversely marginal portion 9b is generated between these outer end portion 31 and first outer sheet 31 as the tape fastener 16 is pulled in the direction of the arrow A. However, it is unlikely that the tape fastener 16 might fall off from the diaper 1 even if the tape fastener is forcefully pulled because the first tape section 51 has its outer end portion 51b bonded to the spots 15 presenting film-like outer surfaces by means of the first adhesive 61. Now it is assumed that the first tape section 51 is placed more aside toward the center line P-P than in the illustrated embodiment and bonded to the nonwoven fabric zone of the first outer sheet 31 but not to the spots 15. In this case, texture of the nonwoven fabric may be destroyed as the tape fastener 16 is forcefully pulled. In other words, the intertwined component fibers constituting the nonwoven fabric and being in contact with the first adhesive 61 may be disentangled and plucked off from the nonwoven fabric zone until the tape fastener 16 may fall off from the diaper 1. Such problem is due to a fact that an adhesive strength between the first adhesive 61 and those fibers is sufficiently high to disentangled the intertwined component fibers constituting the outer sheet 31. The problem can not be solved merely by adjusting the adhesive strength provided by the first adhesive 61 but it is rather preferred to make such adjustment, if necessary, only after the first tape section 51 has been bonded to the bonding spots 15.

Figure 4:
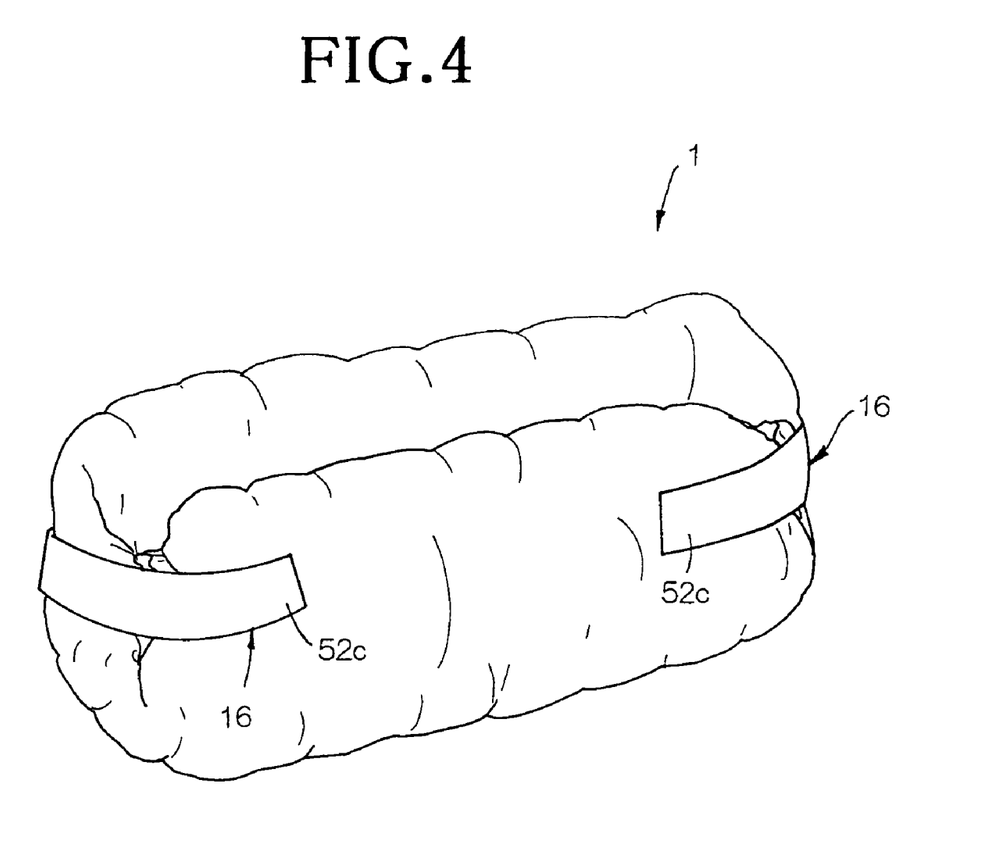
FIG. 4 is a perspective view showing the used diaper having been rolled up for disposal.

FIG. 4 is a perspective view showing the used diaper 1 having been rolled up for disposal. The tape fastener 16 is adapted to be unfolded from the state in FIG. 3 with the finger-grip 52 held by the fingers and then to be fixed to a selected position on the diaper 1 by means of the second adhesive 62. Utilizing such feature, it is preferred to fasten the diaper 1 in its rolled up state with the tape fasteners 16 immediately after the diaper 1 has been used, as illustrated. The tape fastener 16 is useful also to pick up any slack of the diaper 1 in the waist-surrounding direction appearing after the diaper 1 has been put on the wearer. Specifically, the tape fastener 16 may be extended in the waist-surrounding direction so as to tuck the diaper 1 and thereby to pick up the slack. The second adhesive 62 is used in this manner not only as a fastening means but also as a means to keep the tape fastener 16 in Z-shape as seen in FIG. 2. Therefore, an adhesive force of the second adhesive 62 may be adjusted so as to achieve these intended purposes. For example, an adhesive force of the second adhesive 62 used for the purpose as illustrated by FIG. 4 may be sufficiently high to allow the tape fastener 16 to be permanently bonded to a target spot or appropriately low to allow the tape fastener 16 to be temporarily bonded to the target spot. Referring to FIG. 2, the inner surface m of the third tape section 53 facing the second adhesive 62 may be previously coated with suitable surface treatment to facilitate the second adhesive 62 to be peeled off.

Figure 5:
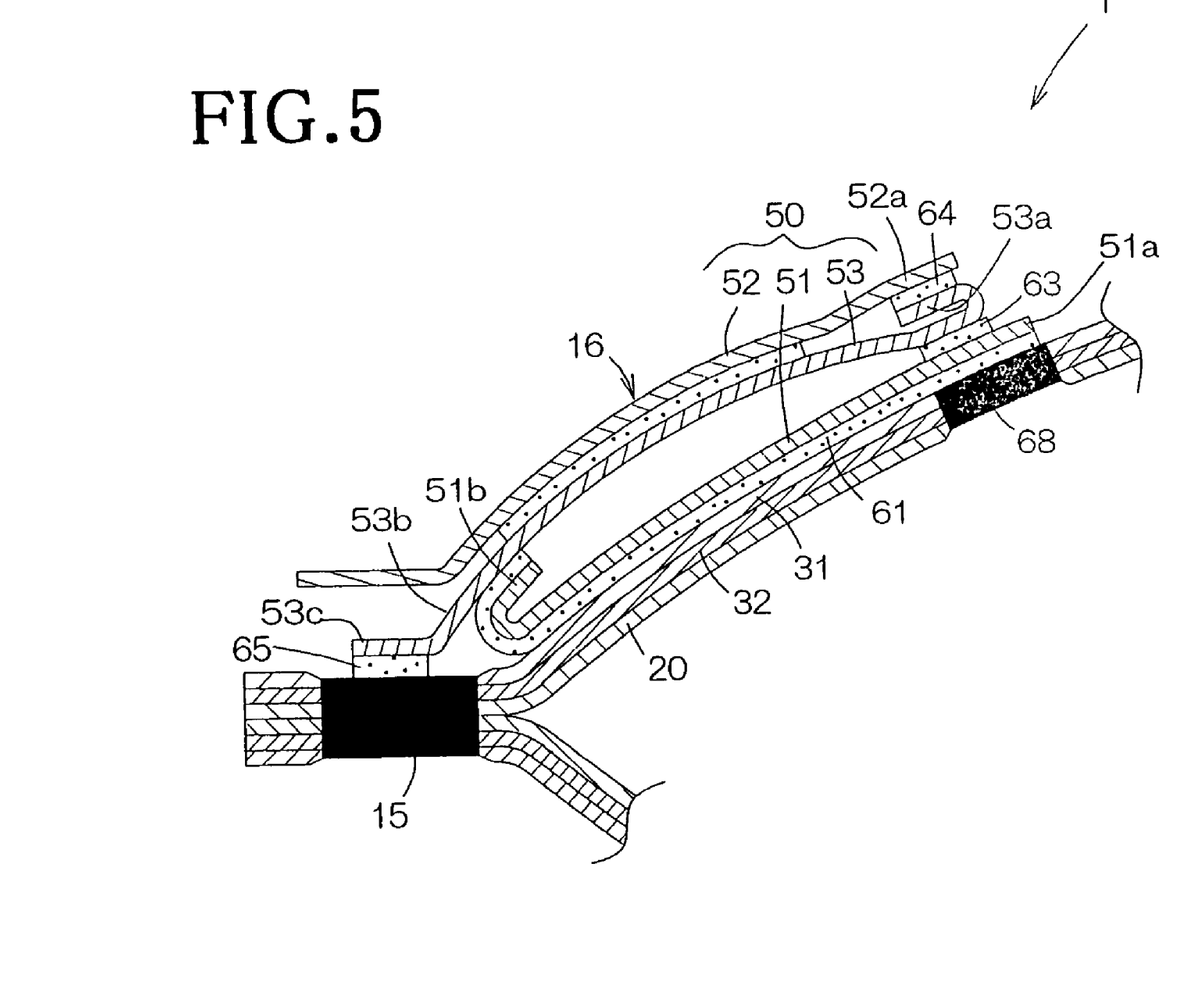
FIG. 5 is a view similar to FIG. 2, showing one preferred embodiment of the invention.

FIG. 5 is a view similar to FIG. 2, showing one preferred embodiment of the invention. In this embodiment, a tape strip 5b constituting each of tape fasteners 16 for diaper 1 comprises three separate tape strips, i.e., a first tape section 51, a second tape section 52 and a third tape section 53. An outer end portion 51b of the first tape section 51 is folded back and permanently bonded to an outer end portion 53b of the third tape section 53 by means of first adhesive 61. An inner end portion 53a of the third tape section 53 is temporarily bonded to an inner end portion 51a of the first tape section 51 by means of third adhesive 63, on one hand, and partially folded back and permanently bonded to an inner end portion 52a of the second tape section 52 by means of fourth adhesive 64, on the other hand. The outer end portion 53b of the third tape section 53 further extends outward to define a distal end portion 53c which extends, in turn, beyond the outer end portion 51b of the first tape section 51 and is permanently bonded to bonding spots 15 having film-like outer surface by means of fifth adhesive 65. The inner end portion 51a of the first tape section 51 is permanently bonded to a film-like spot 68 formed on the first outer sheet 31 by means of first adhesive 61. The film-like spot 68 refers to a portion of the nonwoven fabric constituting the first outer sheet 31 which has been transformed to the film-like state in the substantially same manner as in the case of the bonding spots 15. More specifically, the inner sheet 20, the first outer sheet 31 and the second outer sheet 32 may be heated under a pressure or sonic sealed to fuse these sheets 20, 31, 32 together. There is no anxiety that component fibers of the first outer sheet 31 might be plucked off by the first adhesive 61 as well as the fifth adhesive 65 and the tape fastener 16 might fall off from the diaper 1 as the tape fastener 16 is pulled even when both the first adhesive 61 and the fifth adhesive 65 have a relatively high adhesive force. As illustrated in FIGS. 2 and 5, in a region of the tape strip 50 facing the first outer sheet 31, at least one of this region's ends opposed in the waist-surrounding direction is preferably bonded to the first outer sheet 31 at the film-like spot 68.

Figure 6:
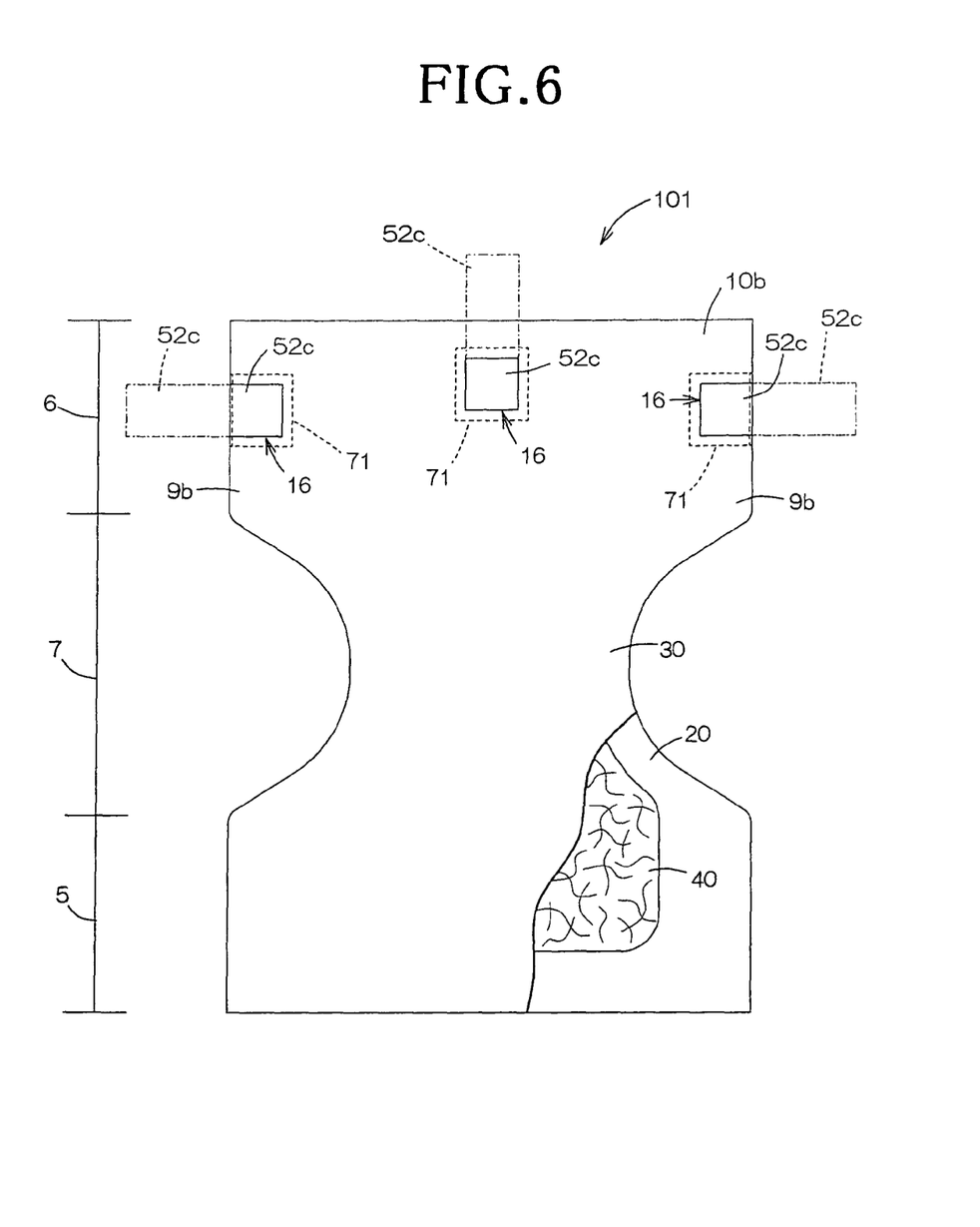
FIG. 6 is a partially cutaway plan view showing an open-type diaper as another preferred embodiment of the invention.

FIG. 6 is a partially cutaway plan view showing an open-type diaper 101 as another preferred embodiment of the invention. The diaper 101 comprises a liquid-pervious inner sheet 20 formed from a nonwoven fabric of thermoplastic synthetic fibers, a substantially liquid-impervious outer sheet 30 formed from a nonwoven fabric of thermoplastic synthetic fibers and a liquid-absorbent core 40 interposed between these two sheets 20, 30. As for the configuration, the diaper 101 is composed of a crotch region 7, a front waist region 5 extending forward from the crotch region 7 and a rear waist region 6 extending rearward from the crotch region 7. Transversely opposite lateral edge portions 9b of the rear waist region 6 and a transversely middle spot of the rear waist region 6 in the vicinity of its upper end portion 10b are provided with the tape fasteners 16 similar to those used in the embodiment illustrated by FIG. 2, respectively. These tape fasteners 16 are adapted to be unfolded and thereby to be extended outward from the diaper 101 as indicated by imaginary lines by pulling these tape fasteners 16 with respective finger-grips 52c. Spots of the outer sheet 30 defined inside respective imaginary lines 71 are heated under a pressure so that nonwoven fabric of the outer sheet 30 in these regions may be transformed to a film-like state. The tape fasteners 16 are bonded to these regions by means of the first adhesive 61 (See FIG. 2) and therefore it is not apprehended that texture of the outer sheet 30 might be destroyed and the tape fasteners 16 might fall off from the diaper 101 even when the tape fasteners 16 are forcefully pulled. When the tape fastener 16 is attached to the rear waist region 6 in the vicinity of its upper end portion 10b, the inner and outer sheets 20, 30 may be welded to each other continuously or intermittently along the upper end portion 10b between the transversely opposite lateral edge portions 9b to ensure that the outer sheet 30 is locally transformed to the film-like state, and thereafter the tape fastener 16 may be bonded to the film-like spot obtained in this manner.

Without departing from the scope of the present invention, the first outer sheet 31 comprising a nonwoven fabric used in the embodiment shown by FIG. 2 as well as the outer sheet 30 used in the embodiment shown by FIG. 6 may be transformed to the film-like state in any spots so far as these spots are to be provided with the tape fasteners. The fastening means formed by the first adhesive in the embodiments having been described heretofore may be replaced by a hook member, one of components constituting together with a loop member so-called mechanical fastener, which is adapted to be anchored on the nonwoven fabric forming the first outer sheet 31. When this hook member is used as the fastening means, the outer surface n of the third tape section 53 shown in FIG. 2 is formed preferably using a nonwoven fabric so that the second tape section 52 can be temporarily fixed to the outer surface n of the third tape section 53. The present invention is applicable not only to the disposable diaper having been described heretofore but also to the other wearing articles such as training pants and pants for incontinent patient.

The present invention makes it possible to mass-produce the wearing article free from the anxiety that the tape fasteners might fall off from the article.

What is claimed is:

1. A disposable wearing article, comprising:
    a crotch region;
    a front waist region extending forward in a longitudinal direction of said article from said crotch region;
    a rear waist region extending rearward in the longitudinal direction from said crotch region;
    each of said regions having a pair of transversely opposite lateral edge portions extending in the longitudinal direction;
    each of said front and rear waist regions further including an end portion extending in a transverse direction of said article between the lateral edge portions thereof;
    at least one tape fastener attached to an outer surface of said article in one of said lateral edge portions of one of said front and rear waist regions; and
    an adhesive fastening element provided on said tape fastener and releasably engageable with the outer surface of said article;
    wherein
    said outer surface of said one of said front and rear waist regions is defined by a nonwoven fabric made of thermoplastic synthetic fibers;
    said tape fastener is bonded to a bonding region of said nonwoven fabric by means of an adhesive layer;
    said bonding region of said nonwoven fabric comprises a plurality of said synthetic fibers fused together;
    said front and rear waist regions are bonded together at a plurality of heat-sealed spots arranged along the respective lateral edge portions of said waist regions to define a waist hole and two leg holes;
    in each of said heat-sealed spots, a number of said fused synthetic fibers are fused together;
    said adhesive layer is disposed between, directly contacts and permanently bonds at least one of said heat heat-sealed spots and said tape fastener, said at least one of said heat-sealed spots defining said bonding region;
    said nonwoven fabric comprises a further bonding region, wherein said further bonding region comprises a number of said synthetic fibers fused together and is spaced inwardly from said bonding region by a section of said nonwoven fabric which is free of the fused synthetic fibers;
    said adhesive layer is disposed between, directly contacts and permanently bonds said further bonding region and said tape fastener; and
    said tape fastener is bonded to said nonwoven fabric in a folded state in which the fastening element is located between and releasably attaches an upper fold and a lower fold of said tape fastener to hold said tape fastener in the folded state, and
    said lower fold of said tape fastener comprises:
        opposite ends permanently bonded to said bonding region and said further bonding region, respectively, and
        a middle portion located between said opposite ends and bonded to said section of said nonwoven fabric by said adhesive layer.

2. The disposable wearing article according to claim 1, wherein
    said at least one tape fastener comprises a pair of tape fasteners respectively attached to the lateral edge portions of said one of said waist regions, and
    each said tape fastener is folded in a Z-shape, is unfoldable from said Z-shape, and includes three separate tape strips including a first tape strip, a second tape strip and a third tape strip connected together.

3. The wearing article according to claim 2, wherein said at least one of said heat-sealed spots includes a single layer film in which the respective lateral edge portions of said waist regions are fused together.

4. The wearing article according to claim 3, wherein said single layer film extends through an entire thickness of each of the respective lateral edge portions of said waist regions and is present on outermost surfaces of both said waist regions.

5. The wearing article according to claim 4, wherein each of the respective lateral edge portions of said waist regions comprises multiple layers of non-woven fabric or plastic films all of which are fused together in said single layer film so as to be indistinguishable one layer from another in said single layer film.

6. The wearing article according to claim 5, wherein said fused synthetic fibers no longer retain their fibrous nature in said single layer film.

7. The wearing article according to claim 6, wherein the synthetic fibers retain their fibrous nature outside said single layer film where said synthetic fibers are adhesively bonded to said tape fastener.

8. The wearing article according to claim 1, wherein
    said one of said front and rear waist regions further comprises an inner sheet different from said nonwoven fabric which is an outer sheet; and
    said inner sheet defines an inner surface of said one of said front and rear waist regions and is made of a thermoplastic synthetic material which is fused together with the synthetic fibers of said outer sheet in said further bonding region.

9. The wearing article according to claim 1, wherein said fused synthetic fibers define a film-like surface.

10. The wearing article according to claim 1, wherein said at least one of said heat-sealed spots includes a single layer film in which the respective lateral edge portions of said waist regions are fused together and which is free of material of the fastening element of said tape fastener.

11. The wearing article according to claim 10, wherein said single layer film extends through an entire thickness of each of the respective lateral edge portions of said waist regions and is present on the outer surfaces outermost surfaces of both said waist regions.

12. The wearing article according to claim 10, wherein each of the respective lateral edge portions of said waist regions comprises multiple layers of non-woven fabric or plastic films all of which are fused together in said single layer film so as to be indistinguishable one layer from another in said single layer film.

13. The wearing article according to claim 10, wherein said fused synthetic fibers no longer retain their fibrous nature in said single layer film.

14. The wearing article according to claim 13, wherein the synthetic fibers retain their fibrous nature outside said single layer film where said synthetic fibers are bonded to said tape fastener by said adhesive layer.

* * * * *